(12) United States Patent
Ascher et al.

(10) Patent No.: US 7,569,587 B2
(45) Date of Patent: Aug. 4, 2009

(54) ANTIBACTERIAL MUTILINS

(75) Inventors: Gerd Ascher, Kundl (AT); Heinz Berner, Vienna (AT); Johannes Hildebrandt, Oeynhausen (AT)

(73) Assignee: Nabriva Therapeutics AG, Vienna (AT)

( * ) Notice: Subject to any disclaimer, the term of this patent is extended or adjusted under 35 U.S.C. 154(b) by 31 days.

(21) Appl. No.: 11/652,812

(22) Filed: Jan. 12, 2007

(65) Prior Publication Data

US 2007/0135483 A1 Jun. 14, 2007

Related U.S. Application Data

(62) Division of application No. 10/363,840, filed as application No. PCT/EP01/10502 on Sep. 11, 2001, now Pat. No. 7,169,804.

(30) Foreign Application Priority Data

| Sep. 13, 2000 | (GB) | ................... | 0022439.4 |
| Sep. 13, 2000 | (GB) | ................... | 0022440.2 |
| Oct. 9, 2000  | (GB) | ................... | 0024674.4 |

(51) Int. Cl.
*A61K 31/445* (2006.01)
*C07D 211/06* (2006.01)

(52) U.S. Cl. ...................... 514/319; 546/195
(58) Field of Classification Search ................. 546/195; 514/319
See application file for complete search history.

(56) References Cited

U.S. PATENT DOCUMENTS

| 4,278,674 A | 7/1981 | Egger et al. |
| 4,675,330 A | 6/1987 | Berner et al. |
| 6,020,368 A | 2/2000 | Hinks et al. |
| 6,281,226 B1 | 8/2001 | Berry et al. |

FOREIGN PATENT DOCUMENTS

| DE | 2811314 | 3/1978 |
| EP | 0013768 | 8/1980 |
| WO | WO 99/21855 | 5/1999 |
| WO | WO 00/27790 | 5/2000 |
| WO | WO 00/37074 | 6/2000 |
| WO | WO 01/09095 | 2/2001 |

OTHER PUBLICATIONS

Byrn et al., Solid-State Chemistry of Drugs, Second Edition, 1999, pp. 233-247.*

* cited by examiner

*Primary Examiner*—Rebecca L Anderson
(74) *Attorney, Agent, or Firm*—D. Peter Hochberg; Sean F. Mellino; Daniel J. Smola

(57) ABSTRACT

A compound of formula (I) wherein R and $R_2$ and the attached nitrogen atom form pyrrolidinyl or piperidinyl. $R_1$ is a group of formula (II). $R_3$ and $R'_3$ are hydrogen, deuterium or halogen. $R_4$, $R_5$ and $R_{10}$ are independently of each other hydrogen or alkyl. $R_6$, $R_7$ and $R_8$ are hydrogen or deuterium. $R_9$ is amino, alkyl, aryl, heterocyclyl or mercapto. If X is oxygen, $R_9$ is additionally hydrogen; $R'_{10}$ is alkyl, X is sulphur, oxygen, $NR_{10}$, or $N+(R'_{10})_2$; Y is sulphur or oxygen, and m is 0,1 or 2, with the proviso that, when R and $R_2$ and the attached nitrogen atom form piperidinyl, m is O, Y is S and Y is attached in position 3 of the piperidine ring, that group of formula (I) which is attached to the piperidine ring via the residue Y is either in the (S)-configuration or in the (R)-configuration, preferably in the (S)-configuration which is useful as antimicrobial, antibacterial.

4 Claims, No Drawings

ANTIBACTERIAL MUTILINS

CROSS REFERENCE TO RELATED APPLICATIONS

This application is a divisional application of application Ser. No. 10/363,840, filed on Mar. 10, 2003 and issued as U.S. Pat. No. 7,169,804 on Jan. 30, 2007, which is a National Stage application of International Application No. PCT/EP2001/10502, filed on Sep. 11, 2001, which claims priority of United Kingdom Application No. 0022440.2, filed on Sep. 13, 2000, United Kingdom Application No. 0022439.4, filed on Sep. 13, 2000 and United Kingdom Application No. 0024674.4, filed on Oct. 9, 2000.

The present invention relates to compounds having e.g. antimicrobial, such as antibacterial, activity; more specifically the present invention relates to mutilins.

In one aspect the present invention provides a compound of formula

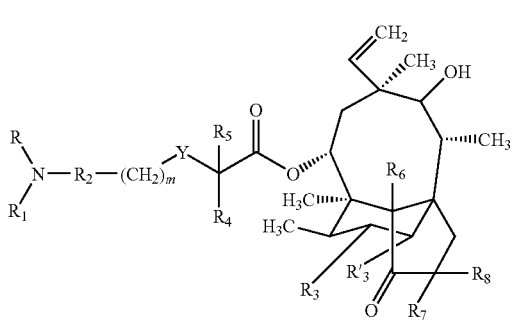

wherein
R and $R_2$ together with the nitrogen atom to which they are attached form pyrrolidinyl or piperidinyl,
$R_1$ is a group of formula

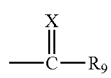

$R_3$ and $R'_3$ are hydrogen, deuterium or halogen,
$R_4$ is hydrogen or alkyl, e.g. $(C_{1-4})$alkyl,
$R_5$ is hydrogen or alkyl, e.g. $(C_{1-4})$alkyl,
$R_6$, $R_7$ and $R_8$ are hydrogen or deuterium;
$R_9$ is amino, alkyl, aryl, heterocyclyl or mercapto; and, if X is oxygen, $R_9$ is additionally hydrogen;
$R_{10}$ is hydrogen or alkyl, e.g. $(C_{1-4})$alkyl,
$R'_{10}$ is alkyl, e.g. $(C_{1-4})$alkyl,
X is sulphur, oxygen, $NR_{10}$, or $N^+(R'_{10})_2$ e.g. in the presence of an appropriate anion;
Y is sulphur or oxygen, and
m is 0, 1 or 2;
with the proviso that, when R and $R_2$ together with the nitrogen atom to which they are attached form piperidinyl, m is 0, Y is S and Y is attached in position 3 of said piperidine ring that group of formula I which is attached to the piperidine ring via the residue Y is either in the (S)-configuration or in the (R)-configuration, preferably in the (S)-configuration, e.g. with the proviso that, when R and $R_2$ together with the nitrogen atom to which they are attached form piperidinyl, m is 0, Y is S and Y is attached in position 3 of said piperidine ring, a part of $R_9$ is either in the (S)-configuration or in the (R)-configuration, e.g., if $R_9$ is alkyl substituted by amino, that amine group is either in the (S)-configuration or in the (R)-configuration; e.g. with the proviso that, if in a compound of formula I m is 0, a part of formula I is either in the (S)-configuration or in the (R)-configuration, e.g. if $R_9$ is alkyl substituted by amino, that amine group is either in the (S)-configuration or in the (R)-configuration.

An anion in a group of formula $N^+(R'_{10})_2$ includes appropriate anions, e.g. anions as conventional in an ammonium group as a counterion.

In a compound of formula I
$R_3$, $R'_3$, $R_4$, $R_5$, $R_6$, $R_7$ and $R_8$ are preferably hydrogen;
R and $R_2$ together with the nitrogen atom to which they are attached form pyrrolidine or piperidine (with the proviso as indicated above), e.g. unsubstituted pyrrolidine or piperidine (beside being substituted by a group of formula —C(=X)$R_9$), or substituted pyrrolidine or piperidine (further subsituted beside being substituted by a group of formula —C(=X)$R_9$), e.g. substituted by one or more groups which are conventional in organic chemistry, e.g. pleuromutilin chemistry. Preferably pyrrolidine or piperidine are unsubstituted (beside being substituted by a group of formula —C(=X)$R_9$)). In a compound of formula I pyrrolidine and piperidine include a group —N($R_1$) and are bound to a group —$(CH_2)_m$—Y. The group —N($R_1$) and the group —$(CH_2)_m$—Y may be vicinal or in another position in the pyrrolidine or piperidine ring, e.g. in positions 1,2; 1,3; 1,4; 1,5, and, in case of piperidine, 1,6; and are preferably in positions 1,3 or 1,4 in case of the piperidine ring and in positions 1,2 or 1,3 in case of the pyrrolidine ring;
$R_9$ is preferably alkyl, e.g. $(C_{1-8})$alkyl, such as $(C_{1-4})$alkyl, e.g. unsubstituted or substituted alkyl, e.g. substituted by groups which are conventional in pleuromutilin chemistry, e.g. one or more amino, heterocyclyl, e.g. including a 5 or 6 membered ring containing 1 or 2 nitrogen atoms; e.g. imidazolyl. If $R_9$ is alkyl substituted by amino, e.g. and heterocyclyl, $R_9$ is preferably that part of an amino acid which remains if the carboxylic group is split off, e.g. the group —C(=X)— wherein X is oxygen can be regarded as the carbonyl part of said amino acid;
X is preferably oxygen;
Y is preferably sulphur, and
m is preferably 0 or 1.

If not otherwise defined herein heterocyclyl includes a 5 or 6 membered ring having 1 to 4 heteroatoms selected from S, O and N; e.g. N; optionally condensed with a further ring (system), e.g. condensed with a phenyl ring; e.g. or condensed with a heterocyclyl ring. Heterocyclyl includes unsubstituted or substituted heterocyclyl, e.g. substituted by groups which are conventional in organic chemistry, e.g. pleuromutilin chemistry. Alkyl includes $(C_{1-8})$alkyl, e.g. $(C_{1-4})$alkyl. Aryl includes phenyl. Amino includes a free amine group, alkyl- and dialkylamine.

In another aspect the present invention provides a compound of formula I, wherein
$R_3$, $R'_3$, $R_4$, $R_5$, $R_6$, $R_7$ and $R_8$ are hydrogen;
$R_1$ is a group of formula

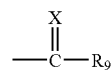

R and $R_2$ together with the nitrogen atom to which they are attached form piperidine or pyrrolidine; $R_9$ is alkyl; X is oxygen; Y is sulphur; and m is 0 or 1;

with the proviso that, when R and $R_2$ together with the nitrogen atom to which they are attached form piperidinyl, m is 0, Y is S and Y is attached in position 3 of said piperidine ring, that group of formula I which is attached to the piperidine ring via the residue Y is either in the (S)-configuration or in the (R)-configuration, preferably in the (S)-configuration;

e.g. with the proviso that, when R and $R_2$ together with the nitrogen atom to which they are attached form piperidinyl, m is 0, Y is S and Y is attached in position 3 of said piperidine ring, a part of $R_9$ is either in the (S)-configuration or in the (R)-configuration, e.g. if $R_9$ is alkyl substituted by amino, that amine group is either in the (S)-configuration or in the (R)-configuration;

e.g. with the proviso that, if in a compound of formula I m is 0, a part of formula I is either in the (S)-configuration or in the (R)-configuration, e.g. if $R_9$ is alkyl substituted by amino, that amine group is either in the (S)-configuration or in the (R)-configuration.

In another aspect the present invention provides a compound of formula

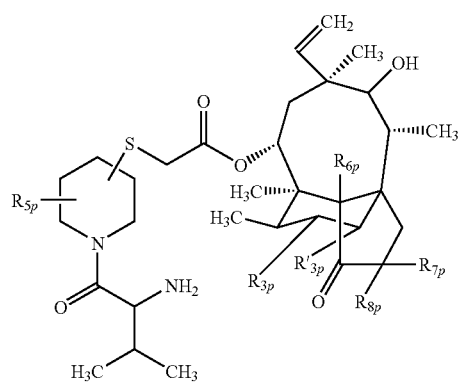

$I_p$ wherein $R_{3p}$, $R'_{3p}$, $R_{6p}$, $R_{7p}$ and $R_{8p}$ are, index-number correspondingly, as defined above for $R_3$, $R'_3$, $R_6$, $R_7$ and $R_8$; and $R_{5p}$ is hydrogen or one or more substituents, preferably hydrogen; and if the group attached to the piperidine ring via the sulphur atom is in position 3 of said piperidine ring and $R_{5p}$ is hydrogen, then the group attached to the sulphur atom is either in the (S)-configuration or in the (R)-configuration, preferably in the (S)-configuration;

e.g. with the proviso that in the group attached to the nitrogen atom of the piperidine ring, the amine group is either in the (S)-configuration or in the (R)-configuration.

In another aspect the present invention provides a compound of formula

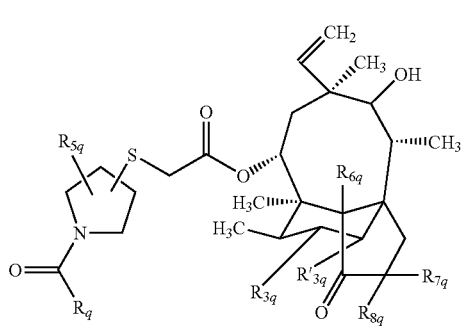

$I_q$ wherein $R_{3q}$, $R'_{3q}$, $R_{6q}$, $R_{7q}$ and $R_{8q}$ are, index-number correspondingly, as defined above for $R_3$, $R'_3$, $R_6$, $R_7$ and $R_8$; $R_{5q}$ is hydrogen or one or more substituents, preferably hydrogen; and $R_q$ is is that part of an amino acid which remains if the carboxylic group is split off; e.g. including a compound of formula

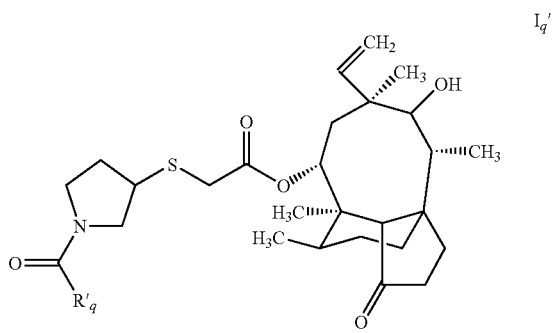

$I'_q$ wherein $R'_q$ is as defined above for $R_q$, e.g. with the proviso that in a group $R_q$, or $R'_q$, respectively, the amine group of the amino acid residue is either in the (S)-configuration or in the (R)-configuration.

In another aspect the present invention provides a compound of formula

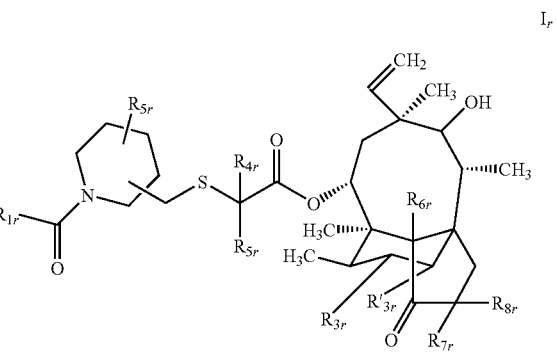

$I_r$ and of formula

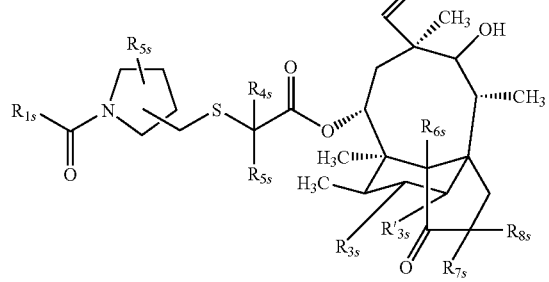

$I_s$ wherein $R_{3r}$, $R'_{3r}$, $R_{6r}$, $R_{7r}$ and $R_{8r}$, or $R_{3s}$, $R'_{3s}$, $R_{6s}$ $R_{7s}$ and $R_{8s}$, respectively, are, index-number correspondingly, as defined above for $R_3$, $R'_3$, $R_6$, $R_7$ and $R_8$;

$R_{5r}$ or $R_{5s}$, respectively, is hydrogen or one or more substituents, preferably hydrogen; and $R_{1r}$ or $R_{1s}$, respectively, is that part of an amino acid which remains if the carboxylic group is split off; e.g. wherein in a compound of formula $I_r$ the group attached to the piperidine ring via the sulphur atom is either in the (S)-configuration or in the (R)-configuration; e.g.

wherein in a group $R_{1r}$ or $R_{1s}$, respectively, the amine group of the amino acid residue is either in the (S)-configuration or in the (R)-configuration.

In another aspect the present invention provides the compound, e.g. a compound selected from the group consisting of, 14-O—[(N-(3-Methyl-2-amino-buturyl-piperidin-3(S)-yl)sulfanyl)acetyl]mutilin, e.g. including 14-O—[(N-(3-Methyl-2(R)-amino-buturyl-piperidin-3(S)-yl)sulfanyl)acetyl]mutilin; and 14-O—[(N-(3-Methyl-2(S)-amino-buturyl-piperidin-3(S)-yl)sulfanyl)acetyl]mutilin;

14-O—[(N-(3-Methyl-2-amino-buturyl-piperidin-4-yl)sulfanyl)acetyl]mutilin, e.g. including 14-O—[(N-(3-Methyl-2(R)-amino-buturyl-piperidin-4-yl)sulfanyl)acetyl]mutilin, and 14-O—[(N-(3-Methyl-2(S)-amino-buturyl-piperidin-4-yl)sulfanyl)acetyl]mutilin;

14-O—[(N-(3-Methyl-2-amino-butyryl)-piperidin-3-yl)-methylsulfanylacetyl]-mutilin, e.g. including 14-O—[(N-(3-Methyl-2-amino-butyryl)-piperidine-3(S)-yl)-methylsulfanylacetyl]-mutilin, and 14-O—[(N-(3-Methyl-2-amino-butyryl)-piperidine-3(R)-yl)-methylsulfanylacetyl]-mutilin, such as 14-O—[(N-(3-Methyl-2(S)-amino-butyryl)-piperidine-3(S)-yl)-methylsulfanylacetyl]-mutilin, and 14-O—[(N-(3-Methyl-2(R)-amino-butyryl)-piperidine-3(S)-yl)-methylsulfanylacetyl]-mutilin;

14-O—[(N-(3-Methyl-2-amino-butyryl)-pyrrolidine-2-yl)-methylsulfanylacetyl]-mutilin, e.g. including 14-O—[(N-(3-Methyl-2-amino-butyryl)-pyrrolidine-2(R)-yl)-methylsulfanylacetyl]-mutilin, and 14-O—[(N-(3-Methyl-2-amino-butyryl)-pyrrolidine-2(S)-yl)-methylsulfanylacetyl]-mutilin, such as 14-O—[(N-(3-Methyl-2(R)-amino-butyryl)-pyrrolidine-2(R)-yl)-methylsulfanylacetyl]-mutilin and 14-O—[(N-(3-Methyl-2(S)-amino-butyryl)-pyrrolidine-2(R)-yl)-methylsulfanylacetyl]-mutilin, 14-O—[(N-(3-Methyl-2-amino-butyryl)-pyrrolidin-3-yl)sulfanylacetyl]mutilin, e.g. including 14-O—[(N-(3-Methyl-2(R)-amino-butyryl)-pyrrolidine-3-yl)-sulfanylacetyl]-mutilin and 14-O—[(N-(3-Methyl-2(S)-amino-butyryl)-pyrrolidine-3-yl)-sulfanylacetyl]-mutilin; and 14-O—[(N-histidinyl-pyrrolidin-3-yl)sulfanylacetyl]mutilin, e.g. including 4-O—[(N—(R)-histidinyl-pyrrolidin-3-yl)sulfanylacetyl]mutilin, and 4-O—[(N—(S)-histidinyl-pyrrolidin-3-yl)sulfanylacetyl]mutilin.

e.g. in free form or in the form of a salt, e.g. a salt with hydrochloric acid; such as a hydrochloride.

14-O—[(N-histidinyl-pyrrolidin-3-yl)sulfanylacetyl]mutilin is 14-O—[(N-(3-(imidazol-4yl)-2-amino-propionyl-pyrrolidin-3-yl)sulfanylacetyl]mutilin.

Compounds provided by the present invention are hereinafter designated as "compound(s) of the present invention". A compound of the present invention includes a compound in any form, e.g. in free form, in the form of a salt, in the form of a solvate and in the form of a salt and a solvate. A compound of formula I includes a compound of formula $I_p$, $I_q$, $I_q'$, $I_r$ and $I_s$.

In another aspect the present invention provides a compound of formula I in the form of a salt, or in the form of a salt and in the form of a solvate, or in the form of a solvate.

A salt of a compound of formula I includes a pharmaceutically acceptable salt, e.g. including a metal salt or an acid addition salt. Metal salts include for example alkali or earth alkali salts; acid addition salts include salts of a compound of formula I with an acid, e.g. hydrogen fumaric acid, fumaric acid, naphthalin-1,5-sulphonic acid, hydrochloric acid, deuterochloric acid; preferably hydrochloric acid or deuterochloric acid.

A compound of formula I in free form may be converted into a corresponding compound in the form of a salt; and vice versa. A compound of formula I in free form or in the form of a salt and in the form of a solvate may be converted into a corresponding compound in free form or in the form of a salt in unsolvated form; and vice versa.

A compound of the present invention may exist in the form of isomers and isomeric mixtures thereof, e.g. optical isomers, cis trans configurated isomers. A compound of the present invention may e.g. contain asymmetric carbon atoms and may thus exist in the form of diastereoisomeres and mixtures thereof, e.g. epimers. For example in a compound of formula I, that group bound via group —$(CH_2)_m$—Y to the pyrrolidine or piperidine ring may be in the (R)- and in the (S)-configuration, e.g. including mixtures thereof. E.g. if $R_9$ is alkyl substituted by amine, e.g. $R_9$ is that part of an amino acid which remains if the carboxylic group is split off, said amine group in $R_9$ may be in the (S)- or in the (R)-configuration, e.g. including mixtures thereof.

Isomeric, diastereoisomeric and epimeric mixtures may be separated as appropriate, e.g. according to a method as conventional, to obtain pure isomers. Pure isomers may also be produced as appropriate, e.g. according, e.g. analogously, to a method as conventional, e.g. or as described herein.

The present invention includes a compound of the present invention in any isomeric form and in any isomeric mixture, with the proviso that, when R and $R_2$ together with the nitrogen atom to which they are attached form piperidinyl, m is 0, Y is S and Y is attached in position 3 of said piperidine ring, that group of formula I which is attached to the piperidine ring via the residue Y is either in the (S)-configuration or in the (R)-configuration, preferably in the (S)-configuration;

e.g. with the proviso that, when R and $R_2$ together with the nitrogen atom to which they are attached form piperidinyl, m is 0, Y is S and Y is attached in position 3 of said piperidine ring, a part of $R_9$ is either in the (S)-configuration or in the (R)-configuration, e.g. if $R_9$ is alkyl substituted by amino, that amine group is either in the (S)-configuration or in the (R)-configuration;

e.g. with the proviso that, if in a compound of formula I m is 0, a part of formula I is either in the (S)-configuration or in the (R)-configuration, e.g. if $R_9$ is alkyl substituted by amino, that amine group is either in the (S)-configuration or in the (R)-configuration.

Preferably the configuration in the mutilin ring of a compound of formula I is the same as in a naturally produced mutilin.

A compound of the present invention may be obtained as appropriate, e.g. according, e.g. analogously, to a method as conventional, or, as described herein.

In another aspect the present invention provides a process for the production of a compound of formula I as defined above comprising the steps a. reacting a compound of formula

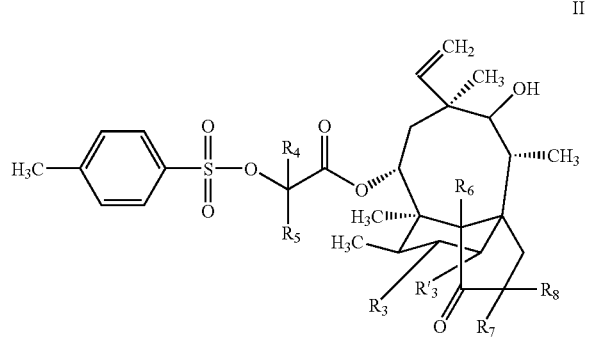

II wherein $R_3$, $R'_3$, $R_4$ and $R_5$ are as defined above and $R_6$, $R_7$ and $R_8$ are hydrogen, with urea or thiourea and subsequent reduction to obtain a compound of formula

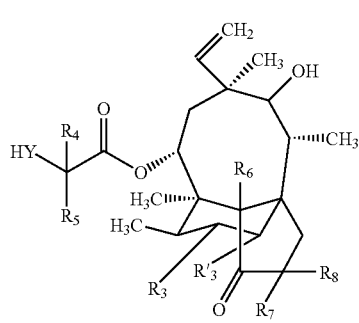

III wherein Y is as defined above; $R_3$, $R'_3$, $R_4$ and $R_5$ are as defined above and $R_6$, $R_7$ and $R_8$ are hydrogen, b. reacting a compound of formula III as defined in step a. with optionally substituted pyrrolidine, methyl or ethyl pyrrolidine, piperidine, methyl or ethyl piperidine (=methyl-, ethyl-pyrrolidine or piperidine), respectively, carrying at the nitrogen atom a group of formula —C(=X)$R_9$, wherein X and $R_9$ are as defined above, in the form of a reactive derivative, e.g. in the form of a mesylate or a tosylate; to obtain a compound of formula

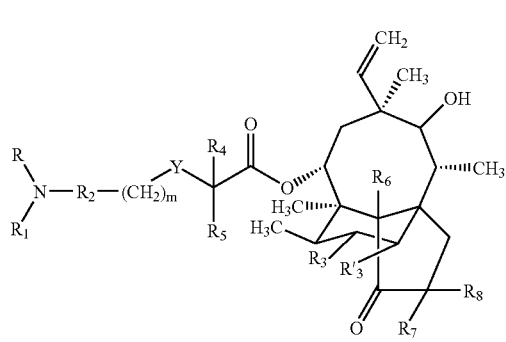

IV which is a compound of formula I wherein R, $R_1$, $R_2$, $R_3$, $R'_3$, $R_4$, $R_5$, Y and m are as defined above and $R_6$, $R_7$ and $R_8$ are hydrogen; and, if desired, c. introducing deuterium into a compound of formula IV as defined in step b, to obtain a compound of formula I, wherein R, $R_1$, $R_2$, $R_3$, $R'_3$, $R_4$, $R_5$, Y and m are as defined above and $R_6$, $R_7$ and $R_8$ are deuterium.

Groups may be unprotected or protected and may be deprotected in any step, if desired, e.g. according, e.g. analogously to a method as conventional.

E.g. in an optionally substituted pyrrolidine, methyl or ethyl pyrrolidine, piperidine, methyl or ethyl piperidine (=methyl-, ethyl-pyrrolidine or piperidine), respectively, carrying at the nitrogen atom a group of formula —C(=X)$R_9$, wherein $R_9$ is alkyl substituted by amine, said amine group may be protected or unprotected. Appropriate protection groups include e.g. protection groups as conventional, such as tert.butoxycarbonyl (BOC).

If in step b. as defined above the methane- or toluenesulphonic acid residue, respectively, attached to the methyl-, ethyl-pyrrolidine or piperidine ring is in the (R)-configuration a compound of formula W obtained may be in a form, wherein the group attached to the methyl-, ethyl-pyrrolidine or piperidine ring via the sulphur atom is in the (S)-configuration; If in step b. as defined above the methane- or toluenesulphonic acid residue, respectively, attached to the methyl-, ethyl-pyrrolidine or piperidine ring is in the (S)-configuration a compound of formula IV obtained may be in a form, wherein the group attached to the methyl-, ethyl-pyrrolidine or piperidine ring via the sulphur atom is in the (R)-configuration (Walden inversion).

If in step b. as defined above in a group of formula —C(=X)$R_9$ attached to the methyl-, ethyl-pyrrolidine or piperidine ring used for reaction with a compound of formula III $R_9$ is alkyl substituted by amine, e.g. that part of an amino acid which remains if the carboxylic group is split off, wherein said amine is in the (R)-configuration, a compound of formula IV is obtained, wherein said amine is in the (R)-configuration. If in step b. as defined above in a group of formula —C(=X)$R_9$ attached to the methyl-, ethyl-pyrrolidine or piperidine ring used for reaction with a compound of formula III $R_9$ is alkyl substituted by amine, e.g. that part of an amino acid which remains if the carboxylic group is split off, wherein said amine is in the (S)-configuration, a compound of formula IV is obtained, wherein said amine is in the (S)-configuration.

The production of a compound of formula I, wherein $R_3$ and $R'_3$ are deuterium or halogen may be e.g. carried out via treatment of a compound of formula

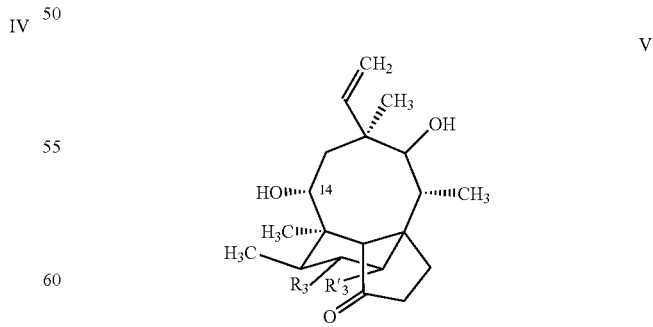

V wherein the carbon atoms carrying $R_3$ and $R'_3$, which both are hydrogen, together form a double bond with deuterium or halogen, e.g. $F_2$, $Cl_2$, $Br_2$, to obtain a compound of formula V, wherein $R_3$ and $R'_3$ are deuterium or halogen; and further reacting a compound of formula V as appropriate to obtain a compound of formula I wherein $R_3$ and $R'_3$ are deuterium or halogen.

Preferably a compound of formula II may be obtained from a compound of formula V by reacting a compound of formula V with a compound of formula

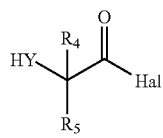

VI wherein Y, $R_4$ and $R_5$ are as defined above and Hal is halogen, preferably bromo, chloro. Introduction of deuterium in a compound of formula I may be carried out by treatment of a compound of formula I, wherein $R_6$, $R_7$ and $R_8$ are hydrogen, e.g. in the form of a hydrochloride, with deuterochloric acid (DCl) in appropriate solvent (system); and isolation of a compound of formula I wherein $R_6$, $R_7$ and $R_8$ and are deuterium. If a compound of formula I is in the form of an acid addition salt, such as a hydrochloride, treatment of said salt with DCl may also result in the replacement of the hydrogen of said acid, e.g. in a compound of formula I in the form of a deuterochloride.

Any compound described herein, e.g. compounds of formula II, III, IV, V, VI and optionally substituted pyrrolidines, methyl or ethyl pyrrolidines, piperidines, methyl or ethyl piperidines, respectively, are known or may be obtained according, e.g. analogously, to a method as conventional, e.g. or as described herein.

The compounds provided by the present invention including compounds of formula I, hereinafter designated as "active compound(s) of the present invention" exhibit pharmacological activity and are therefore useful as pharmaceuticals. For example, the active compounds of the present invention, e.g. compounds of the examples, show antimicrobial, e.g. antibacterial, activity against gram positive bacteria, such as Staphylococci, e.g. *Staphylococcus aureus*, Streptococci, e.g. *Streptococcus pyogenes, Streptococcus pneumoniae*, Enterococci, e.g. *Enterococcus faecium*, as well as against *Mycoplasms, Chlamydia* and obligatory anaerobes, e.g. *Bacteroides fragilis*; in vitro in the Agar Dilution Test or Microdilution Test according to National Committee for Clinical Laboratory Standards (NCCLS) 1997, Document M7-A4 Vol. 17, No. 2: "Methods for dilution Antimicrobial Susceptibility Tests for Bacteria that Grow Aerobically—Fourth Edition, Approved Standard"; and in the Anaerobic Bacteria TEST according to National Committee for Clinical Laboratory Standards (NCCLS) VOL. 13, No. 26, M11-A4, Methods for Antimicrobial Susceptibility Testing of Anaerobic Bacteria; Approved Standard; Fourth Edition (1997).

The active compounds of the present invention show antibacterial activity in vitro (MIC (μg/ml)) in the Agar Dilution Test or in the Microdilution Test from about ≦0.01 μg/ml to 25 μg/ml, e.g. against above mentioned bacterial species; and are active against Mycoplasms and Chlamydia. MIC=minimal inhibitory concentration.

The active compounds of the present invention show e.g. activity in systemic infections of mice determined according to the Handbook of animal models of infection. Edition Oto Zak and Merle A. Sande, Academic Press, 1999), e.g. against *Staphylococcus*, e.g. when administered parenterally or orally, e.g. at dosages from about 5 to 150 mg/kg body weight;

e.g. the $ED_{50}$ values for the compounds 14-O—[(N—(R)-histidinyl-pyrrolidin-3 -yl)sulfanylacetyl]mutilin or 14-O—[(N-(3-methyl-2(R)-amino-butyryl)-pyrrolidine-3-yl)-sulfanylacetyl]-mutilin is of about 11.0 mg/kg body weight; and the $ED_{50}$ values for the compound 14-O—[(N-(3-methyl-2 (R)-amino-buturyl)-piperidin-3(S)-yl)sulfanyl)acetyl]-mutilin, is in the range of 7.0 mg/kg body weight.

$ED_{50}$=Effective dosage in mg/kg body weight per application by which 50% of the treated animals are protected from death; calculated by Probit analysis (n=8 animals/group).

In another aspect the present invention provides a compound of the present invention for use as a pharmaceutical, preferably as an antimicrobial, such as an antibiotic, e.g. and as an anti-anaerobic.

In another aspect the present invention provides a compound of the present invention for use in the preparation of a medicament for the treatment of microbial diseases, for example of diseases caused by bacteria, e.g. selected from Staphylococci, Streptococci, Enterococci; e.g. and of diseases caused by *Mycoplasms, Chlamydia* and obligatory anaerobes.

Surprisingly the active compounds of the present invention show also activity against strains which are resistant against erythromycin(s), tetracycline(s), e.g. strains including penicillin or multidrug-resistant strains, e.g. of *Staphylococcus aureus* (MRSA).

In another aspect the present invention provides a method of prophylaxis and treatment of microbial diseases which comprises administering to a subject in need of such treatment an effective amount of a compound of the present invention, e.g. in the form of a pharmaceutical composition.

For prophylaxis and treatment of microbial diseases, the appropriate dosage will, of course, vary depending upon, for example, the active compound of the present invention employed, the host, the mode of administration and the nature and severity of the conditions being treated. However, in general, for satisfactory results in larger mammals, for example humans, an indicated daily dosage is in the range from about 0.5 to 3 g, of an active compound of the present invention conveniently administered, for example, in divided doses up to four times a day.

An active compound of the present invention may be administered by any conventional route, preferably orally, e.g. in form of tablets, powders, capsules, suspensions; e.g. including non-resorbable oral formulations; or parenterally, e.g. in the form of injectable solutions or suspensions; or topically, e.g. in the form of nasal sprays, body solutions, creams, eye drops. The active compounds of the present invention may be administered in analogous manner, e.g. in similar doses and for similar indications, as erythromycin(s), tetracycline(s).

The active compounds of the present invention may be administered in the form of a pharmaceutically acceptable salt, e.g. an acid addition salt or metal salt;

or in free form; optionally in the form of a solvate. The active compounds of the present invention in the form of a salt exhibit the same order of activity as the active compounds of the present invention in free form.

In another aspect the present invention provides a pharmaceutical composition comprising a compound of the present invention in free form or in the form of a pharmaceutically acceptable salt; e.g. and/or in the form of a solvate; in association with at least one pharmaceutical carrier or diluent.

Such compositions may be manufactured according, e.g. analogously, to a method as conventional. Unit dosage form may contain, for example, about 100 mg to about 1 g.

The active compounds of the present invention are additionally suitable as veterinary agents, e.g. veterinary active compounds, e.g. in the prophylaxis and in the treatment of microbial, e.g. bacterial diseases, in animals, such as fowl, pigs and calves; e.g. and for diluting fluids for artificial insemination and for egg-dipping techniques.

In another aspect the present invention provides a compound of the present invention for use as a veterinary agent.

In another aspect the present invention provides a compound of the present invention for the preparation of a veterinary composition which is useful as a veterinary agent e.g. in the prophylaxis and in the treatment of microbial, e.g. bacterial diseases, in animals.

The present invention further provides a veterinary method for the prophylaxis and the treatment of microbial, e.g. bacterial, diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 3 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton.

It is preferred to administer the active compounds of the present invention as a veterinary agent to hens in drinking water, to pigs in foodstuff and to calves orally or parenterally, e.g. in the form of oral or parenteral preparations.

In the following examples which illustrate the invention temperatures are in degree Celsius and are uncorrected.

The following abbreviations are used:
BOC: tert.butoxycarbonyl
TFA: trifluoroacetic acid
DCC: dicyclohexylcarbodiimide The numbering of the mutilin cyclus referred to in the examples is given in the following formula:

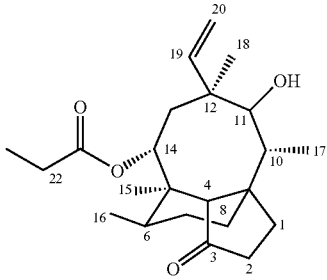

EXAMPLES

Example 1

14-O—[(N-(3-Methyl-2-amino-buturyl-piperidin-3-yl)sulfanyl)acetyl]mutilin

A) 14-O-[(Carbamidoylsulfanyl)acetyl]mutilin-tosylate

A solution of 15.2 g of thiourea and 106.4 g of pleuromutilin-22-O-tosylate in 250 ml of acetone is heated under reflux, solvent is removed under reduced pressure and 100 ml of hexane are added. A precipitate forms, is filtrated off and dried.

14-O-[(Carbamidoylsulfanyl)acetyl]mutilin-tosylate is obtained.

B) 14-Mercapto-acetyl-mutilin

A solution of 4.7 g of sodium pyrosulfite ($Na_2S_2O_5$) in 25 ml of $H_2O$ is added to a solution of 12.2 g of 14-O-[(carbamimidoylsulfanyl)acetyl]mutilin-tosylate in a mixture of 20 ml of ethanol and 35 ml of $H_2O$ (warmed to ca. 90°). 100 ml of $CCl_4$ are added to the reaction mixture obtained and the mixture is heated under reflux. The two-phase system obtained is separated, the organic phase is dried and the solvent is evaporated off.

14-Mercapto-acetyl-mutilin is obtained.

C) N—BOC-3(R)-Hydroxy-piperidine

A suspension of 3.48 g of 3-(R)-hydroxypiperidine, 8.72 g of di-tert.butyl-dicarbonat and 4.0 g of N-metyl-morpholine in 70 ml of dioxane is stirred at room temperature. From the mixture obtained the solvent is evaporated off and the evaporation residue is dissolved in $CH_2Cl_2$ and extracted with 1N HCl. The organic phase is dried and the solvent is evaporated off.

5.08 g of N—BOC-3(R)-Hydroxy-piperidine are obtained which can be used without further puification for further reaction.

D) N—BOC-3(R)-methylsulfonyloxy-piperidine

A solution of 5.08 g of N—BOC-3(R)-Hydroxy-piperidine and 8.7 g of methanesulfonic acid anhydride in 100 ml of pyridine is stirred at room temperature. Pyridine is distilled off under high vacuum and the distillation residue obtained is dissolved in $CH_2Cl_2$, which is extracted with 1N HCl. The organic phase obtained is dried and the solvent is evaporated off to dryness. The residue is purified by chromatography.

3.8 g of N—BOC-3(R)-methylsulfonyloxy-piperidine are obtained.

$^1$HNMR ($CDCl_3$): 4.7(m, 1H, $CHOSO_2CH_3$), 3.2-3.6 (m, 4H, CHN), 3.0 (s, 3H, $CH_3SO_2$), 1.4 (m, 9H, tert.butyl).

E) 14-O—[(N—BOC-Piperidin-3(S)-yl)-sulfanylacetyl]-mutilin

A solution of 1.97 g of 22-mercapto-acetyl-pleuromutilin, 1.39 g of N—BOC-3(R)-methyl-sulfonyloxy-piperidine and 0.12 g of sodium in 50 ml of EtOH is heated to 90°. The solvent of the mixture obtained is evaporated off to dryness under vacuum and the residue is subjected to chromatography. 2.5 g of 14-O—[(N—BOC-Piperidin-3(S)-yl)-sulfanylacetyl]-mutilin are obtained.

$^1$HNMR ($CDCl_3$): 6.45, 5.35, 5.2 (3×m, $H_{19}$, $H_{20}$, $H_{21}$), 5.74 (d, 1H, 5.2 Hz, $H_{14}$), 3.35 (d, 1H, $H_{11}$, J=5.2 Hz), AB-system: 3.12,3.18, (J=14.7 Hz, $H_{22}$), 3.2, 2.95, 2.65,2.6 (4×m, $CH_2NCH_2$), 2.85 (m, 1H, SCH), 1.18, 1.45 (2×s, $(CH3)_{15}$, $CH3)_{18}$), 0.75,0.88 (2×d, $(CH_3)_{18}$ $(CH_3)_{17}$, J=5.4 Hz)

F) 14-O—[(N-(3-Methyl-2(R)-amino-buturyl)-piperidin-3(S)-yl)sulfanyl)acetyl]mutilin in the form of a hydrochloride A solution of 280 mg of 14-O—[(N—BOC-Piperidin-3(S)-yl)-sulfanylacetyl]-mutilin in 20 ml methylenchloride and 1 ml TFA is stirred at room temperature for ca. 30 minutes and the solvent of the mixture obtained is evaporated off to dryness. To the evaporation residue obtained, dissolved in 40 ml of $CH_2Cl_2$, 55 mg of N-metylmorpholine, 110 mg of N—BOC—(R)-valine and 105 mg of DCC are added. The mixture obtained is stirred and precipitated dicyclohexylurea is filtrated off. The solvent from the filtrate obtained is evaporated off and the evaporation residue is subjected to chromatography. 14-O—[(N-(3-Methyl-2(R)-(N—BOC-amino)- buturyl)-piperidin-3(S)-yl)sulfanyl)acetyl]mutilin is obtained and is treated with TFA. The solvent of the mixture obtained is evaporated off to dryness and the evaporation residue is treated with etheric HCl. Solid, amorphous 14-O—[(N-(3-methyl-2(R)-amino-buturyl)-piperidin-3(S)-yl)sulfanyl)acetyl]mutilin in the form of a hydrochloride is obtained.

$^1$HMR (d$_6$-DMSO, 330K): 6.45, 5.35, 5.2 (3×m, H$_{19}$, H$_{20}$, H$_{21}$), 5.74 (d, 1H, 5.2 Hz, H$_{14}$), 5.45 (d, 1H, NH, J=7.8 Hz), 4.1 (m, 1H, NHCHCO), 3.35 (d, 1H, H$_{11}$, J=5.2 Hz), AB-system: 3.12, 3.18, (J=14.7 Hz, H$_{22}$), 3.2, 2.95, 2.65, 2.6 (4×m, CH$_2$NCH$_2$), 2.8 (m, 1H, SCH), 1.18, 1.45 (2×s, (CH3)$_{15}$, (CH3)$_{18}$), 0.75, 0.88 (2×d, (CH$_3$)$_{16}$, (CH$_3$)$_{17}$, J=5.4 Hz), 0.78, 0.84 (2×d, (CH$_3$)$_2$CH J=6.8 Hz)

Example 2

14-O—[(N-(3-Methyl-2-amino-buturyl-piperidin-4-yl)sulfanyl)acetyl]mutilin

According to the method described in Example 1 but using the appropriate starting materials (e.g. 4-hydroxymethyl-piperidine instead of 3-hydroxymethyl-piperidine), 4-O—[(N-(3-Methyl-2(R)-amino-buturyl-piperidin-4-yl)sulfanyl) acetyl]mutilin in the form of a hydrochloride is obtained.

$^1$HMR (d$_6$-DMSO): 8.1 (b, 3H, NH3+), 6.2-6.4 (m, 1H, H19), 5.55 (d, 1H, H14), 5.1-5.2 (m, 2H, H20), 4.25 (m, 1H, NCHCO), 4.1,4.25 (m, 1H, NCH), 3.8-3.95 (m, 1H, NCH), 3.4 (d, 1H, H11), 3.0-3.2 (m, 2H, NCH), 2.8-2.95 (m, 1H, sCH), 2.4 (m1H, H4), 3.25-3.4 (m, 2H, SCH2CO), 1.08, 1.39 (2×s, (CH3)15, (CH3)18), 0.93,0.98 (2×d, 6H, (CH3)2CH), 0.65,0.85 (2×d, 6H, (CH3)16, (CH3)16, (CH3)17).

Example 3

14-O—[(N-(3-Methyl-2-amino-butyryl)-piperidin-3-yl)-methylsulfanylacetyl]-mutilin A) N—BOC-3(R)-Hydroxymethyl-piperidine A suspension of 3.48 g of 3-(R)-hydroxymethyl-piperidine, 8.72 g of di-tert.butyl-dicarbonat and 4.0 g of N-methylmorpholine in 70 ml of dioxane is stirred for ca. 18 hours at room temperature. From the mixture obtained the solvent is evaporated off and the evaporation residue is dissolved in CH$_2$Cl$_2$ and extracted with 1N HCl. The organic phase is dried and the solvent is evaporated off. 5.08 g of N—BOC-3 (R)-hydroxymethyl-piperidine are obtained which may be used for further reaction without further puification.

B) N—BOC-3(R)-Methylsulfonyloxymethyl-piperidine

A solution of 5.08 g of N—BOC-3(R)-hydroxymethyl-piperidine and 8.7 g of methanesulfonic acid anhydride in 100 ml of pyridine is stirred at room temperature for ca. 22 hours. From the mixture obtained pyridine is evaporated off (high vacuum) and the evaporation residue obtained is dissolved in CH$_2$Cl$_2$. The organic phase obtained is extracted with 1N HCl, dried and the solvent is evaporated off. The evaporation residue is subjected to chromatography. 3.8 g of N—BOC-3 (R)-methylsulfonyloxymethyl-piperidine are obtained.

C) 14-O—[(N—BOC-Piperidin-3(S)-yl)-methylsulfanylacetyl]-mutilin

A solution of 1.97 g of 22-mercapto-pleuromutilin, 1.39 g of N—BOC-3(R)-methylsulfonyloxymethyl-piperidine and 0.12 g of sodium in 50 ml of EtOH is heated at ca. 90°. The solvent of the mixture obtained is evaporated off and the evaporation residue obtained is subjected to chromatography. 2.5 g of 14-O—[(N—BOC-Piperidin-3(S)-yl)-methylsulfanylacetyl]-mutilin are obtained.

D) 14-O—[(N-(3-Methyl-2(S)-amino-butyryl)-piperidine-3(S)-yl)-methylsulfanylacetyl]-mutilin in the form of a hydrochloride A solution of 280 mg of 14-O—[(N—BOC-piperidin-3 (S)-yl)-methylsulfanylacetyl]-mutilin in 20 ml of CH$_2$Cl$_2$ and 1 ml of TFA is stirred at room temperature for ca. 30 minutes and the solvent of the mixture obtained is evaporated off. The evaporation residue obtained is dissolved in 40 ml of CH$_2$Cl$_2$ and to the solution obtained 55 mg of N-metylmorpholine, 110 mg of N—BOC—(S)-valine and 105 mg of DCC are added and the mixture obtained is stirred. From the mixture obtained a solid (precipitated dicyclohexylurea) is filtrated off and the filtrate obtained is subjected to chromatography. 14-O—[(N—BOC-(3-Methyl-2(S)-amino-butyryl)-piperidine-3(S)-yl)-methylsulfanylacetyl]-mutilin is obtained which is treated with TFA and etheric HCl. 14-O—[(N-(3-Methyl-2(S)-amino-butyryl)-piperidine-3(S)-yl)-methylsulfanylacetyl]-mutilin in the form of a hydrochloride is obtained.

$^1$HNMR (d$_6$-DMSO): 6.1-6.2 (m, 1H, H19), 5.58 (d, 1H, H14). 5.5-5.12 (m, 2H, H20), 4.2 (m, 2H, NCHCO, NCH), 3.75 (m, 1H, NCH), 3.42 (d, 1H, H11), 3.28-3.35 (m, 2H, SCH$_2$CO), 3.1 (m, 2H, SCH$_2$), 1.08,1.36 (2×s, 6H (CH$_3$)$_{15}$, (CH$_3$)$_{18}$), 0.95,0.98 (2×d, 6H, (CH$_3$)$_2$CH), 0.65,0.83 (2×d, 6H (CH$_3$)$_{16}$, (CH$_3$)$_{17}$.

Example 4

14-O—[(N-(3-methyl-2-amino-butyryl)-pyrrolidine-2-yl)-methylsulfanylacetyl]-mutilin According to the method described in Example 3 but using the appropriate starting materials (e.g. 2-(S)-hydroxymethyl-pyrrolidine instead of 3-(R)-hydroxymethyl-piperidine and N—BOC—(R)-valine instead of N—BOC—(S)-valine); 14-O—[(N-(3-methyl-2(R)-amino-butyryl)-pyrrolidine-2 (R)-yl)-methylsulfanylacetyl]-mutilin in the form of a hydrochloride is obtained.

$^1$HNMR (d$_6$-DMSO): Rotamere, 8.1 (b, 3H, NH3), 6.1-6.2 (m, 1H, H19), 5.52 (d, 1H, H14), 5.5-5.12 (m, 2H, H20), 4.15 (m, 1H, NCHCO), 3.9 (m, 1H, NCH), 3.6 (m, 1H, NCH), 3.42 (d, 1H, H11), 3.28-3.35 (m, 2H, SCH$_2$CO), 2.68,2.85 (2×dd, 2H, CHCH$_2$S), 1.08,1.36 (2×s, 6H (CH$_3$)$_{18}$), 0.95,0.98 (2×d, 6H, (CH$_3$)$_2$CH), 0.65,0.83 (2×d, 6H (CH$_3$)$_{16}$, (CH$_3$)$_{17}$.

Example 5

14-O—[(N-(3-Methyl-2-amino-butyryl)-pyrrolidin-3-yl)sulfanylacetyl]mutilin

According to the method described in Example 1 but using appropriate starting materials, e.g. N—BOC-3(R)-methylsulfonyloxy-pyrrolidine instead of N—BOC-3(R)-methylsulfonyloxy-piperidine, 14-O—[(N-(3-methyl-2(R)-amino-butyryl)-pyrrolidine-3-yl)-sulfanylacetyl]-mutilin in the form of a hydrochloride is obtained.

$^1$HNMR (d$_6$-DMSO, 330K): 6.45,5.35,5.2 (3×m,H$_{19}$,H$_{20}$, H$_{21}$), 5.64 (d, 1H, 5.2 Hz,H$_{14}$), 6.3, (b, 1H, NH), 3.95 (m, 1H, NHCHCO), 3.35 (d, 1H, H$_{11}$, J=5.2 Hz), AB-system: 3.0, 3.1, (J=14.7 Hz,H$_{22}$), 3.2, 2.95, 2.65, 2.6 (4×m,CH$_2$NCH$_2$), 2.8

(m, 1H, SCH), 1.18, 1.45, (2×s, (CH3)$_{15}$, (CH3)$_{18}$), 0.75, 0.88 (2×d, (CH$_3$)$_{16}$, (CH$_3$)$_{17}$, J=5.4 Hz), 0.86, 0.84 (2×d, (CH$_3$)$_2$CH, J=6.8 Hz).

Example 6

14-O—[(N-histidinyl-pyrrolidin-3-yl)sulfanylacetyl] mutilin

According to the method described in Example 1 but using appropriate starting materials, e.g. N,N'—BOC—(R)-histidine instead of N—BOC—(R)-valin, 4-O—[(N—(R)-histidinyl-pyrrolidin-3-yl)sulfanylacetyl]mutilin in the form of a hydrochloride is obtained.

$^1$HNMR (d$_6$-DMSO, 330K): 7.45,6.73 (2×s,histidine), 6.25,5.1,5.2 (3×m,H$_{19}$,H$_{20}$,H$_{21}$), 5.59 (d, 1H, 5.2 Hz,H$_{14}$), 5.45 (d, 1H, NH, J=7.8 Hz), 4.5 (d, 1H, NHCHCO, J=4.5 Hz), 3.6,3.4 (2×m, 2H, NCH$_2$CH2), 3.35 (d, 1H, H$_{11}$, J=5.2 Hz), 3.4 (m, 2H, HisCH$_2$), ABX-system: 3.12,3.68, J=14.1 Hz, 6.5 Hz,NCH$_2$CHS), 3.2,2.95,2.65,2.6 (4×m,CH$_2$NCH$_2$), 2.7 (m, 1H, SCH), 1.18,1.45 (2×s, (CH3)$_{15}$, (CH3)18), 0.75,0.88 (2×d, (CH$_3$)$_{16}$, (CH$_3$)$_{17}$, J=5.4 Hz).

We claim:

1. A compound of formula I$_r$

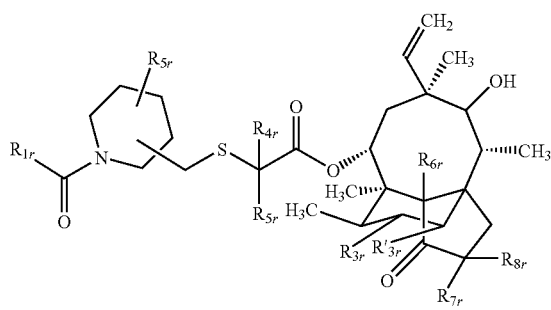

I$_r$ wherein

R$_{3r}$ and R'$_{3r}$ are hydrogen, deuterium, or halogen;

R$_{5r}$ is hydrogen;

R$_{6r}$, R$_{7r}$ and R$_{8r}$ are hydrogen or deuterium; and

R$_{1r}$ is that part of an amino acid which remains if the carboxylic group is split off, or a salt thereof.

2. A compound of claim 1 in the form of a salt.

3. A pharmaceutical composition comprising an effective amount of a compound of claim 1 or a salt thereof and at least one pharmaceutically acceptable carrier or diluent therefor.

4. A pharmaceutical composition of claim 3, wherein a compound of formula I$_r$

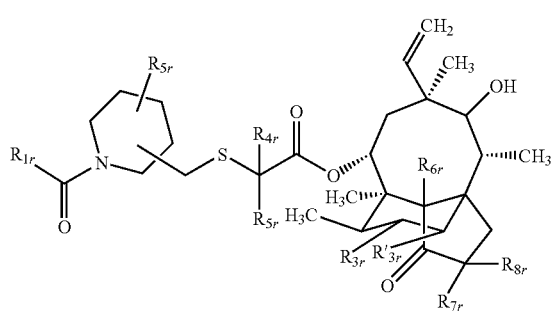

I$_r$ wherein

R$_{3r}$ and R'$_{3r}$ are hydrogen, deuterium, or halogen;

R$_{5r}$ is hydrogen;

R$_{6r}$, R$_{7r}$ and R$_{8r}$ are hydrogen or deuterium; and

R$_{1r}$ is that part of an amino acid which remains if the carboxylic group is split off is in the form of a pharmaceutically acceptable salt.

\* \* \* \* \*